United States Patent
Sunnen et al.

(10) Patent No.: US 9,610,421 B2
(45) Date of Patent: Apr. 4, 2017

(54) DEVICES AND METHOD UTILIZING ULTRA-LOW FREQUENCY NON-VIBRATORY TACTILE STIMULI FOR REGULATION OF PHYSIOLOGICAL PROCESSES

(71) Applicants: Gerard V. Sunnen, New York, NY (US); Martin Sokoloff, New York, NY (US)

(72) Inventors: Gerard V. Sunnen, New York, NY (US); Martin Sokoloff, New York, NY (US)

( * ) Notice: Subject to any disclaimer, the term of this patent is extended or adjusted under 35 U.S.C. 154(b) by 204 days.

(21) Appl. No.: 14/484,997

(22) Filed: Sep. 12, 2014

(65) Prior Publication Data

US 2015/0073313 A1    Mar. 12, 2015

Related U.S. Application Data

(60) Provisional application No. 61/960,168, filed on Sep. 12, 2013.

(51) Int. Cl.
*A61M 21/00* (2006.01)
*A61M 21/02* (2006.01)
*A61N 5/06* (2006.01)

(52) U.S. Cl.
CPC ..... *A61M 21/02* (2013.01); *A61M 2021/0022* (2013.01); *A61M 2021/0027* (2013.01); *A61M 2021/0033* (2013.01); *A61M 2021/0044* (2013.01); *A61M 2205/502* (2013.01); *A61M 2209/088* (2013.01); *A61N 5/0622* (2013.01)

(58) Field of Classification Search
CPC ... A61M 21/00; A61H 23/02; A61H 23/0254; A61H 2023/0209
USPC ...................................... 600/26–28
See application file for complete search history.

(56) References Cited

U.S. PATENT DOCUMENTS

| | | |
|---|---|---|
| 6,001,073 A | 12/1999 | Schmidt et al. |
| 7,282,036 B2 | 10/2007 | Masuda |
| 7,510,537 B2 | 3/2009 | Imboden et al. |
| 8,092,355 B2 | 1/2012 | Mortimer et al. |
| 2005/0043653 A1 | 2/2005 | Trimmer et al. |
| 2006/0211958 A1 | 9/2006 | Rosenberg et al. |
| 2009/0221943 A1 | 9/2009 | Burbank et al. |

FOREIGN PATENT DOCUMENTS

WO    WO 2008/120897    10/2008

*Primary Examiner* — John Lacyk
(74) *Attorney, Agent, or Firm* — Leason Ellis LLP (57) ABSTRACT

The present devices and methods are configured to utilize ultra-low frequency non-vibratory tactile stimuli for the regulation of physiological processes. In one embodiment, an apparatus configured to generate and apply mechanical stimuli to skin of a user for regulating a physiological process includes a housing having a first surface for placement against the skin and an electro-mechanical actuator disposed within the housing and configured to generate and apply the mechanical stimuli to the skin. The mechanical stimuli comprise ultra-low frequency stimuli that have a frequency between about 2 Hz (two stimuli per second) to about 0.1 Hz (one stimulus every 10 seconds). The mechanical stimuli have sufficient energy so as to engage skin sensory receptors that are configured to convey signals to the nervous system where the stimuli are at least one of consciously perceived and subliminally perceived.

21 Claims, 2 Drawing Sheets

Fig. 4

DEVICES AND METHOD UTILIZING ULTRA-LOW FREQUENCY NON-VIBRATORY TACTILE STIMULI FOR REGULATION OF PHYSIOLOGICAL PROCESSES

CROSS REFERENCE TO RELATED APPLICATION

The present application claims the benefit of U.S. patent application Ser. No. 61/960,168, filed Sep. 12, 2013, which is hereby incorporated by reference in its entirety.

TECHNICAL FIELD

The present invention relates to the regulation of physiological processes, such as sleep and organ activity and more specifically, relates to devices and methods that are configured to utilize ultra-low frequency non-vibratory tactile stimuli for the regulation of such physiological processes.

BACKGROUND

Physiological processes are commonly defined as being the functions and activities of living organisms that support life in single- or multi-cellular organisms from their origin through the progression of life. As one would appreciate there are a number of different physiological processes and there is a desire in a number of different settings to control the regulation of such physiological processes. Such physiological processes can include but are not limited to:

1. The slowing of brain waves
2. The induction of relaxation and sleep
3. The lowering of blood pressure
4. The slowing of heart rate
5. The normalizing of gastro-intestinal peristalsis
6. The pacing and slowing of respiratory rate
7. The modulation of urinary bladder over-activity
8. The alleviation of muscular system over-activity While there have been attempts to control and regulate such physiological processes, there remains a need to provide alternative devices and methods for regulating such physiological processes.

SUMMARY

The present invention is directed to devices and methods that are configured to utilize ultra-low frequency non-vibratory tactile stimuli for the regulation of physiological processes. In one embodiment, an apparatus configured to generate and apply mechanical stimuli to skin of a user for regulating a physiological process includes a housing having a first surface for placement against the skin and an electromechanical actuator disposed within the housing and configured to generate and apply the mechanical stimuli to the skin. The mechanical stimuli comprise ultra-low frequency stimuli that have a frequency between about 2 Hz (two stimuli per second) to about 0.1 Hz (one stimulus every 10 seconds). The mechanical stimuli have sufficient energy so as to engage skin sensory receptors that are configured to convey signals to the nervous system where the stimuli are at least one of consciously perceived and subliminally perceived. The apparatus can be configured to regulating one or more physiological processes by performing one or more of the following actions: (a) slowing of brain waves; (b) inducing relaxation and sleep; (c) lowering of blood pressure; (d) slowing of heart rate; (e) normalizing of gastro-intestinal peristalsis; (f) pacing and slowing of respiratory rate; (g) modulating urinary bladder over-activity; and (h) alleviating muscular system over-activity.

DETAILED DESCRIPTION OF CERTAIN EMBODIMENTS

As mentioned herein, the present invention relates to the field of physiological processes. Physiological processes are commonly defined as being the functions and activities of living organisms that support life in single- or multi-cellular organisms from their origin through the progression of life. Preferably, the devices and methods of the present invention relate to human physiological processes and the regulation thereof.

Some of the physiological processes influenced by ultra-low frequency stimulation find themselves in the province of the capacities of the device herewith described and include, but are not limited to: the slowing of brain waves; the induction of relaxation and sleep; the lowering of blood pressure; the slowing of heart rate; the normalizing of gastro-intestinal peristalsis; the pacing and slowing of respiratory rate; the modulation of urinary bladder over-activity; the alleviation of muscular system over-activity.

In other words, the devices of the present invention are configured to advantageously influence the above physiological processes as well as other physiological processes.

As mentioned herein, the present invention is directed to non-vibratory stimuli. Rhythmical or paced presentation of stimuli is not the same as vibratory stimulation. Vibration, according to Webster's Dictionary represents: "a periodic motion of the particles of an elastic body or medium in alternately opposite directions from the position of equilibrium when that equilibrium has been disturbed."

In contrast, the present invention teaches the presentation of ultra-low frequency rhythmic or paced stimuli to the skin which is, according to the above definition of vibration, not vibratory, in nature since these stimuli neither have a periodic motion, nor do they have a point of equilibrium. Moreover, these stimuli are of such low frequency that they lie below the lower ranges for what is commonly conceived as vibrational. Accordingly, the stimuli used in accordance with the present invention are described as being non-vibratory in nature.

In accordance with the present invention, ultra-low frequencies as described herein refer to those frequencies in a range of 2 Hz (two per second), to 0.1 Hz, or one stimulus every 10 seconds.

Figure 1:
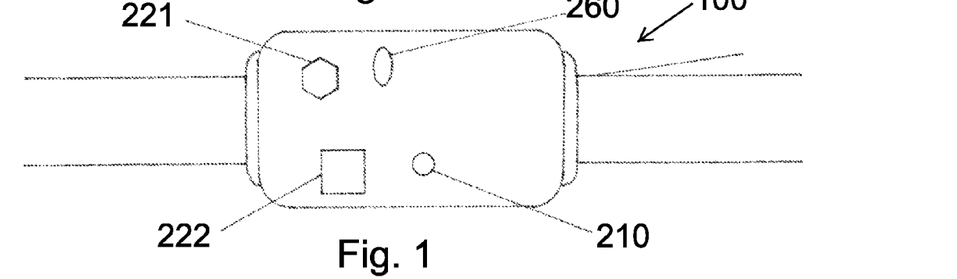
FIG. 1 is a top plan view of a device in accordance with one exemplary embodiment of the present invention and configured to generate ultra-low frequency non-vibratory tactile stimuli for the regulation of physiological processes.
Figure 2:
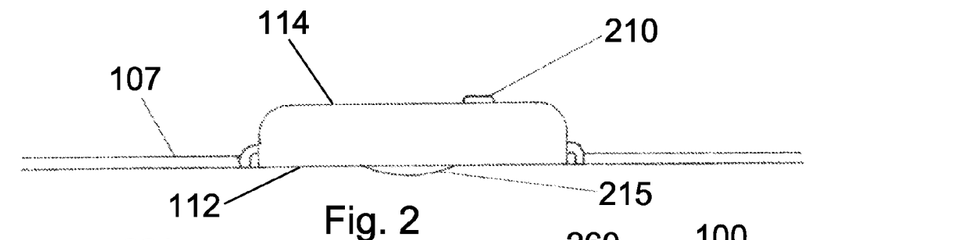
FIG. 2 is a side elevation view thereof.
Figure 3:
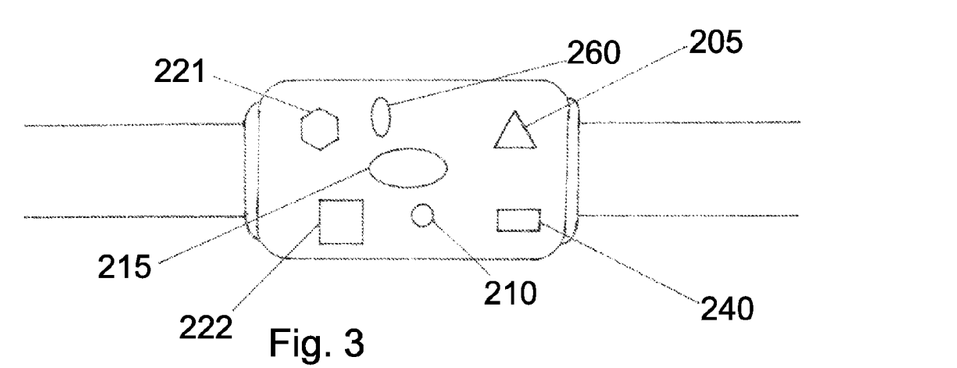
FIG. 3 is a cross-sectional view thereof.

FIGS. 1-3 show one exemplary device 100 according to one exemplary embodiment of the present invention. As described herein, the device 100 can take any number of different forms depending upon different considerations, such as anatomical considerations. In general, the device 100 is configured for placement at a target location of a patient to ensure the proper intimate contact between the device 100 and the skin of the person. The device 100 can thus be of a type that can be detachably attached to the person using any number of different coupling techniques, such as using a mechanical fastener (e.g., the illustrated straps in the figures) or using adhesives (e.g., constructing the device 100 in the form of a patch that has an adhesive section (such as a border) for attachment to the skin of the person or using other suitable techniques.

As shown in FIGS. 1-3, the device 100 includes a housing or casing 110 which contains the operative parts of the device 100 and includes a fastener 105 (fastening means) for attaching the device 100 to a person's body (patient's body). In the exemplary embodiment shown in the figures, the device 100 takes the form of a wearable structure, such as a bracelet or the like, and the fastener 105 is in the form of a pair of straps 107 that engage and mate together so that the device 100 is positioned and maintained at a target location of the person's body. For example, the straps 107 can include conventional buckles or hook and loop material to allow the straps 107 to engage one another and allow the device 100 to be fastened about the person's body (e.g., about a limb).

The housing 110 can take any number of different shapes and sizes depending upon the particular intended application. For example, the housing 110 can have a regular shape, such as a circle, square, oblong shape, rectangular or can have an irregular shape. Other constructions of the housing 110 are described herein.

The housing 110 includes a first face or surface 112 and an opposing second face or surface 114. The first face 112 can be thought of as a lower surface which is a skin contacting surface and the second face 114 can be thought of as being a top surface that faces away from the skin.

As discussed herein, the first face 112 can be formed of more than one material and/or contain more than one section and in particular, the first face 112 can have an active section 215 that is intended to be placed in direct contact with the skin of the person. The active section 215 can be formed of a different material that allows for transmission of the ultra-low frequency stimuli to the skin in the manner described herein and also provides a comfortable interface for the skin. For example, the active section 215 can be formed of a membrane that is formed of a suitable material that freely allows transmission and delivery of the ultra-low frequency stimuli generated by the device 100.

The housing 110 can be formed of any number of suitable materials, including various plastics.

The device has a number of other components, such as a user interface and display and controls as well as a power supply and a means for generating the ultra-low frequency stimuli. Each of these components and others is described in detail below.

In accordance with the present invention, the ultra-low frequency device 100 makes use of the principle of entrainment for modulating physiological processes. Using this concept for slowing the frequency of brain waves, for example, a stimulus frequency is applied corresponding to a desired brain wave frequency. If a subject's brainwaves were currently measured at 10 Hz and the goal was to lower them to 5 Hz, the subject would be presented with a 5 Hz stimulus frequency and, via entrainment, there would hopefully be, in time, a synchronous correspondence of stimulus to brain wave. The foregoing is merely one exemplary application and not limiting of the invention.

In the present invention, the principle developed is what could be called and understood, in addition to entrainment, physiological coaxing and pacing. In this phenomenon, a stimulus may be presented with a much lower frequency than the desired physiological response, so that the said desired response is attained more quickly. While stimuli are generally presented at regular intervals, the present invention also makes possible the presentation of stimuli at irregular or at patterned frequencies. As discussed herein, the user interface associated with the device 100 allows the user to select the operating mode of the device 100 and this can include the manner in which the stimuli are applied (e.g., at what intervals are the stimuli applied).

The method of delivery for these ultra-low frequency stimuli can be via electro-mechanical devices that incorporate solenoids. The properties inherent in this technology is that solenoids have the capacity to generate ultra-low frequency repetitive stimuli, rhythmical or not, while other methods, including those that rely on rotating motors to produce vibrations, cannot. Solenoid electromagnetic technology, for example, can thus deliver impulses to the body that range far below the Delta brain wave frequencies, the lower limit of Delta being 0.5 Hz. The impulses generated by solenoid technology can be programmed to frequencies as low as 0.1 Hz (or one stimulus every 10 seconds), and lower.

Figure 4:
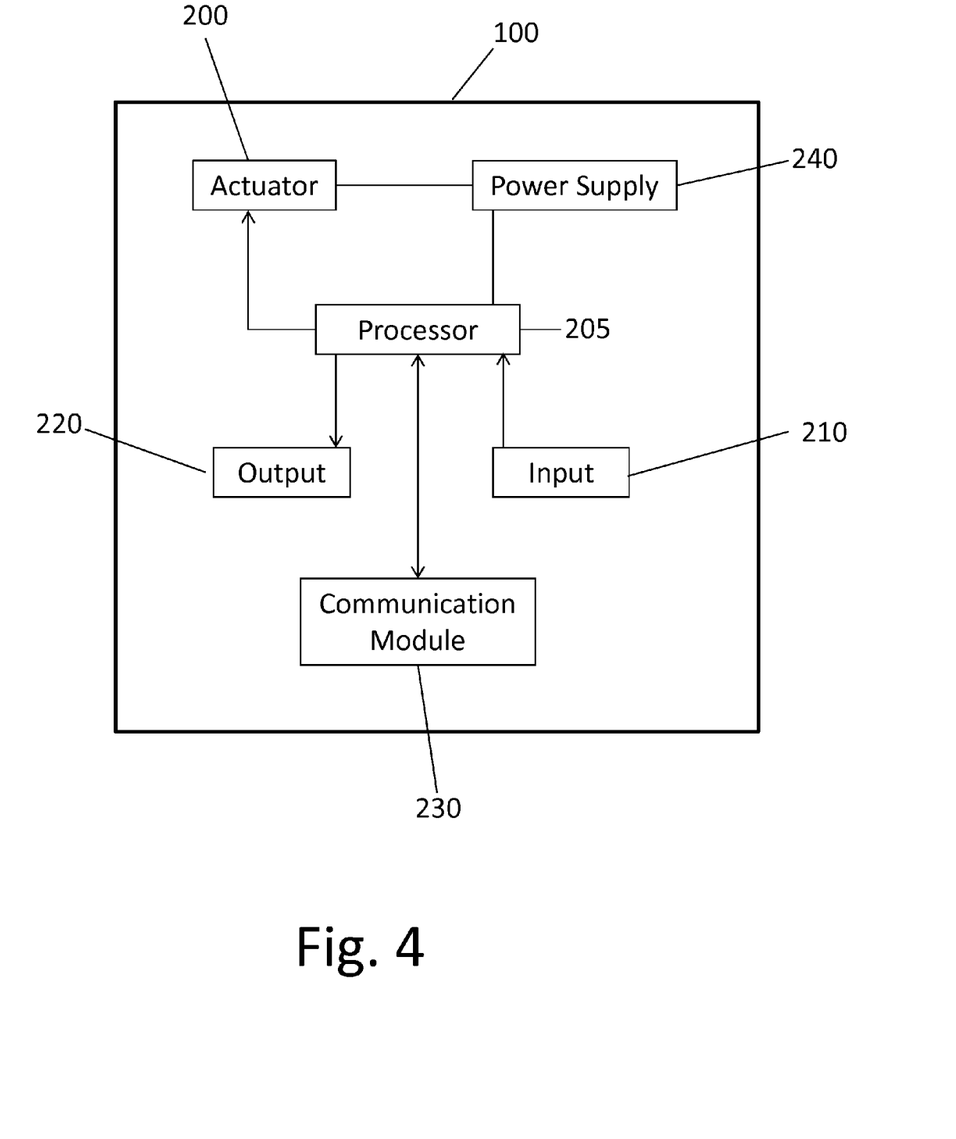
FIG. 4 is a block diagram showing the various components of the device of the present invention.

FIGS. 1-3 illustrate one exemplary ultra-low frequency (ULF) device 100 and FIG. 4 is a block diagram illustrating an exemplary configuration of the device 100 according to an embodiment of the present invention. The device 100 includes various hardware and software components that serve to provide ULF stimuli to a user. The ULF device 100 includes, inter alia, a microprocessor 205 that is communicatively coupled, to a solenoid 200, one or more input devices 210 (e.g., control button and/or touch interface), one or more output devices 220 (e.g., an LED 221 and/or LCD display 222) and a communication interface 230. The ULF device also includes a power source 240 that serves to provide energy to the various components of the device 100, as would be understood by those in the art.

The output device can include a speaker 260 which is configured to emit sound. The rhythm frequency can, in addition to tactile stimuli, generate anyone of a number of sounds, or tones. A menu of pleasing sounds may be chosen (ss by means of the user interface (input device)) such as waterfalls, waves, musical instruments, or electronically generated sounds.

The microprocessor 205 is configured to control the various components of the ULF device 100 and carry out aspects of the systems and methods disclosed herein. The microprocessor 205 can be a number of processors, a multi-processor core, or some other type of processor, depending on the particular implementation. In some implementations the microprocessor 205 is configured by executing one or more software modules that can be loaded into a memory (not shown) and executed by the microprocessor 205. The one or more software modules can comprise one or more software programs or applications having computer program code or a set of instructions executed in the microprocessor 205. Such computer program code or instructions can be written in any combination of one or more programming languages. Preferably, included among the software modules are a user input module, a display module, a stimuli control module and a communication module. During execution of the software modules, the microprocessor 205 configures the ULF device 100 to perform various operations relating to providing ULF stimuli to the user, as will be described in greater detail below.

Memory can be, for example, a random access memory (RAM) or any other suitable volatile or non-volatile computer readable storage medium. In addition, memory can be fixed or removable and can contain one or more components or devices such as a hard drive, a flash memory, a rewritable optical disk, a rewritable magnetic tape, or some combination of the above. In addition memory can be onboard the microprocessor. In addition, it should be noted that other information and/or data relevant to the operation of the present systems and methods can also be stored on memory, as will be discussed in greater detail below.

The electromechanical solenoid 200 is also operatively connected to the microprocessor 205. As would be understood by those in the art, an electromechanical solenoid 200 is an actuator driven by electrical signals. The electromechanical solenoid actuator 200 translates electrical signals received from the microprocessor 205 into mechanical stimuli impacting the skin surface. More specifically, as further described herein, the solenoid 200 is a micro-solenoid that converts the electrical signals into magnetic impulses that physically drive a weight or membrane 215 ("the stimulator") to act upon the skin of the wearer. In some implementations, the stimulator 215 is insulated with a rubberized or plastic envelope, for purposes of noise abatement and user comfort.

It will be appreciated that the stimulator 215 can be fixedly attached to the solenoid 200 itself such that movement of the solenoid 200 results in direct translation (movement) of the stimulator 215. In at least some embodiments, the stimulator 215 can be in the form of a skin that surrounds and intimately contacts the solenoid 200. Movement of the solenoid 200 (as when energized) causes movement of the surrounding or adjacent stimulator 215 (membrane).

One or more light emitting devices 221 (e.g., LED) can also be operatively connected to the microprocessor 200. The LED 221 serves to output information to the user relevant to the operation of the ULF device 100 such as, a device status (e.g., on/off, active/inactive, battery level) and the like. By way of further example, the LED 221 can emit light pulses in synchrony with the stimuli being applied by the UHF device 100.

The display 222 (e.g., LCD display) can also be operatively connected to the microprocessor 200. The display 222 can be a digital display such as a segment display, a dot matrix display or a 2-dimensional display and can incorporate, by way of example and not limitation, a liquid crystal display, light emitting diode display, electroluminescent display and the like. The display 222 provides an output to the user of information relevant to the operation of the ULF device 100, such as the status of the device 100, operating parameters of the device local time, a second time zone, the date, and so on, as a function of the mode of the watch as managed by instructions executing in the microprocessor 200. By way of further example, the display 222 can display the frequency, amplitude and timer functions relating to the stimuli being applied by the UHF device, and related control features. The display 222 can also display the selected time period for application of the stimuli and optionally show a running time indicating the amount of time left for a given application. The time period can vary depending upon the application and can be on the order of less than 1 hr, less than 30 minutes, less than 20 minutes, less than 10 minutes, etc. The foregoing is not an exhaustive list of treatment time periods.

The control button and touch interface represent one or more user input devices that are operatively connected to the microprocessor 200. Such user input devices serve to facilitate the capture commands from the user such as an on-off commands and operating parameters related to the operation of the device, for example, the frequency and amplitude of the tactile stimuli and the duration that the stimuli is administered and other such parameters as further described herein. User input devices can also serve to facilitate the capture of other information from the user and provide the information to the microprocessor.

The control button can be one or more switch(es), button(s), knob(s), key(s). The touch interface is a touch sensitive device that can be is placed in register on the top of the display or on/around the perimeter of the display or anywhere on the housing. A touch interface is comprised of one or more thin, transparent layers that can detect when and where a user touches the interface and it allows a user to interact directly with what is displayed without requiring an intermediate device such as a computer mouse. The touch interface can be constructed using, by way of example and not limited to, resistive, capacitive, acoustic, infrared, optical imaging, or dispersive signal technology.

By way of further example, the touch interface and display can be integrated into a touch screen display. Accordingly, the screen is used to show a graphical user interface, which can display various fields or virtual buttons that allow for the entry of information by the user. Touching the touch screen at locations corresponding to the display of a graphical user interface allows the person to interact with the device to enter data, change settings, control functions, etc. So, when the touch screen is touched, interface communicates this change to microprocessor, and settings can be changed or user entered information can be captured and stored in the memory.

The communication interface 230 can also be operatively connected to the microprocessor 200. The communication interface 230 can be any interface that enables communication between the ULF device 100 and external devices, machines and/or elements including a user's computer system. Communication interface 230 can include but is not limited to a Bluetooth, or cellular transceiver, a radio transceiver, an NFC transceiver, a satellite communication transmitter/receiver, an optical port and/or any other such interfaces for wirelessly connecting the ULF device to an external computing device.

It can be appreciated that aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. For example, the microcontroller can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules can be omitted because the processes for the different embodiments are implemented in a hardware unit.

To augment the neural recruitment of the tactile stimuli generated by the device 100, other stimuli may be paired with them, among them: light, sound, and electro-physiological impulses.

The ultra-low frequency device 100 can be apposed to the skin surface anywhere on the body, and different designs make it possible to appose the device to the wrists—as in a wristband format (see FIGS. 1-3)—or to the ankle, chest, abdomen, and to the head itself, as in a headband.

In one embodiment, the low-frequency stimuli generated and delivered by the device 100 can have an amplitude that is selected between about 0.5 mm to about 5 mm (e.g., between about 0.5 mm to about 3 mm). However, the aforementioned values are only exemplary in nature and not limiting of the present invention since depending upon the construction of the device 100 and/or the application, other amplitudes may be selected.

The Anatomy and Physiology of Sensory Mechanoreceptors.

The device 100, apposed to the skin surface stimulates the sensory organs of the peripheral nervous system. The skin generates a constant flow of information, forwarding it to the spinal cord and to the central nervous system for quasi-instantaneous processing and response. Sensing the shape, temperature, and motion of movements requires skin sensors that quickly translate mechanical energy in the environment into neurological signals.

Skin sensors are micro-organs that inform on texture, pressure, impact, heat, cold, vibration and, importantly, on tissue trauma and inflammation. For the latter, they generate pain signals. Beyond the skin itself, in deeper connective tissues of muscles, tendons and joints, other micro-organs (e.g., spindles) also convey neurological information on body position and motion.

Several types of sensors found in the human skin and in deeper tissues provide a remarkable array of instantaneous information about many of the environment's variegated features:

1. Pacinian corpuscles, found in the dermis, are large by sensor standards and visible to the naked eye. Histologically, they appear as onion-configured concentric lamellae of connective tissue housing unmyelinated nerve roots. The friction of rubbing a finger on a textured object will induce vibratory stimuli registered by Pacinian corpuscles. Their fast adaptation makes them ideal for registering transient touch. Endowed with a large receptive field on the skin surface, they are sensitive to a range of vibrations of 15 to 400 Hz, with an optimal response at approximately 250 Hz.

2. Meissner's corpuscles are encapsulated dermal skin sensors endowed with unmyelinated nerve roots whose adaptive capacities make them optimally responsive to vibrations 50 Hz and below.

3. Merkel's discs respond to minuscule distortions of tissues. Uncapsulated, unmyelinated and extremely sensitive, they are capable of kind of tactile high resolutions needed in Braille. Their optimal vibrational responsiveness ranges between 5 and 15 Hz.

4. Krause's bulbs are minute cylindrical bodies found in superficial skin layers and mucosal tissues. They respond to cold and to low frequency vibrations.

5. Ruffini cylinders are capsulated spindle-shaped receptors found in deeper skin layers. Heat and low frequency vibrations stimulate them.

6. Free nerve endings are unmyelinated neurons abundantly found in the epidermis that transmit signals eventually interpreted as pressure, and pain in any one of its many variations.

The speed of nerve transmission from skin sensors to the spinal cord, and eventually to the brain, depends on the diameter of conducting nerve fibers and on the degree to which they are sheathed in myelin, an insulating complex lipid. The highly myelinated A fibers are large neuronal cables with conduction velocities of 70 to 120 meters/second. They carry sensation of proprioception, touch and pressure. C fibers, on the other hand, thin and unmyelinated, have conduction velocities approximating 1 meter/second. They carry pain sensations.

Sensory fibers with various conduction velocities conveying qualitatively different messages converge to the dorsal columns of the spinal cord, where they ascend to the medulla oblongata, the pons, the midbrain, and on to the thalamus. There, raw sensations gain conscious perception. Thalamic projections forward data to the cortex, where sensations are given subtleties.

Ultra-Low Frequency Stimuli and Physiological Functions

The stimuli generated by the ULF device 100 can be perceived consciously and/or subliminally. Via focused attention, visualization and meditation, this perception may be directed to the organ system in need of modulation. Thus, the stimuli may:

Influence brain wave frequency. In the present invention, the device aims to reduce brain wave frequencies in order to promote relaxation and sleep.

Reduce blood pressure and stabilize heart rate.

Harmonize gastro-intestinal function via the slowing of gastro-intestinal peristalsis.

Stabilize and slow respiratory rate.

Promote muscular relaxation.

Regulate genito-urinary function (slowing bladder activity).

Easing the activity of muscular systems, including the voluntary system (striated muscles), and the autonomic system (smooth muscles).

Slow Brain Waves

ULF topical stimuli may be used to coax brain waves to lower their frequencies. Slow brain waves (SBW) are associated with a large number of physiological, biochemical, and psychological changes, namely:

Relaxation and sleep

Stabilization of blood pressure.

An elevation of mood

Memory consolidation

Improved daytime performance.

Improved glucose metabolism.

Increased cerebral protein synthesis

Increased production of brain gamma-amino butyric acid (GABA)

The production of nitric oxide by certain cortical neurons.

Increased output of pituitary growth hormone

Increased Growth Hormone (GH) output.

Maturation of the cortex during adolescence.

The production of cytokines, thus bolstering immune function.

The physiological, biochemical, and psychological parameters that are influenced by slow brain waves are therefore numerous and diverse, and comprise much more than sleep induction.

The present invention has the capacity to slow down a constellation of bodily processes that include not only brain waves but also cardiovascular, respiratory, gastro-intestinal, muscular, and genito-urinary functions.

The device 100 herewith presented generates repetitive, paced ultra-low frequency tactile stimuli. These tactile stimuli travel within the nervous system, resonating in neural networks, which in turn influence brain pacemakers. Reaching a desired brainwave frequency in a more expeditious way is made possible by presenting the subject with stimulus frequencies much lower than the desired target brainwave frequency. For example, if the target brainwave frequency is 1 Hz, a Delta brainwave associated with sleep, the subject may be presented with a repetitive 0.2 Hz frequency, or one stimulus per 5 seconds. This signals brain sleep pacemakers to activate their innate tendency for synchronicity.

In order to send ultra-low frequency signals to the brain's networks, the device may be positioned on the wrist as a wristband, or on the head, as a headband. In the latter option, the device's solenoid actuator may be placed on selected points on the skull.

Heart Rate Regulation

Many interactive mechanisms determine the circuitry of the autonomic nervous system in its regulation of heart rate and blood pressure.

Baroreceptors are sensors located in the walls of vessels that respond to stretching. As vessels dilate, baroreceptors emit signals that make their way to the medulla oblongada in the brain stem From there, via autonomic nervous system fibers, signals adjust heart rate, cardiac output, blood pressure, and vascular resistance. Other mechanisms involve neuro-humoral networks, the adrenal glands, and the renin-angiotensin system.

The medulla, with its extensive connections to sympathetic and parasympathetic circuits, contains nuclei that also regulate respiration and the reflexes of coughing, pupillary adjustment, salivation, sneezing, swallowing, vomiting, and intestinal movements.

The reticular formation, within the medulla and throughout the brain stem and midbrain, is a yet relatively unexplored massive conglomeration of neurons that, under the microscope, appears as a net (reticulum: net (Greek). The reticular formation receives signal from all body sensors and, importantly, from the most differentiated brain centers, namely the cortical areas, generators of the highest expressions of consciousness.

The medulla's nuclei act as automatic servomechanisms. However, the fact that cortical centers of perception, consciousness and volition have connections to the reticular formation and thus to the medullar networks signifies a role for the conscious control of heart rate and blood pressure, which this device is designed to develop.

Modulating Hypertension

Hypertension poses enormous public health issues. Chronic high blood pressure is well known to be associated with heart attacks (myocardial infarctions), strokes, peripheral vascular disease, kidney disease (nephropathy), and retinal pathology (retinopathy).

Hypertension treatment is best provided using a total patient approach. In this model, all factors affecting high blood pressure are examined and treatment is applied accordingly. A total health assessment looks at all organ systems and, importantly, on life style factors (e.g. dietary and sleep habits, drug and alcohol use, etc.). Medication therapy is usually combined with prescriptions for life style modification. High blood pressure has also been treated with adjunctive psychological techniques including relaxation training, psychotherapy, meditation, hypnosis, and biofeedback.

The present invention proposes a device and method for modulating blood pressure and regulating heart rate, utilizing stimuli that entrain the nervous system toward more peaceful rhythms. Said stimuli are tactile. They, however, can be assisted by the support of auditory, visual, and electrophysiological stimuli. The invention's fundamental concept is that paced ultra-low frequency tactile stimuli have the capacity to regulate, via its reverberating nervous system circuitry, the rhythm of the heart, and the tonicity of the body's vasculature.

The principles of the invention are based on the anatomical fact that neurological circuits extensively cross-communicate. A unifying principle applicable to the nervous system is that every neuron in the body finds connections to every other neuron. This principle is one foundation of this invention. Specifically, a stimulus applied to the skin, will travel throughout nervous system networks, eventually resonating into all cortical and subcortical structures, including the heart rate and blood pressure centers in the nervous system's medulla and brain stem.

One objective of this device 100 is to entrain cardiovascular function to adopt normal parameters of blood pressure and heart rate. The range of the cardiac device's output spans from 1 Hz, or one cycle per second (reflecting an normal healthy heart rate of 60 beats per minute), to 0.2 Hz, or one stimulus per 5 seconds, which coaxes heart rate to normalize more quickly. Optimally, heart rate is most desirable in the range of 55 to 65 beats per minute.

The apparatus 100 and method may also be augmented with synchronous auditory, visual, and electro-physiological stimulation. Multimodal stimuli increase the capacity of the apparatus to regulate the blood pressure and heart rate centers in the nervous system via the involvement of other nervous system pathways and networks.

The device's effectiveness is enhanced by techniques of concentration, visualization and meditation. By lending mindful attention to the experiencing of the device's output, the reprogramming of the nervous system is accelerated, and cardiovascular control is more efficiently achieved.

Regulating Gastro-Intestinal Function

The normal function of the intestinal conduit is associated with rhythmic peristaltic waves of smooth muscle contractions spanning its entire length. These waves are essential for the proper transit and digestion of food. Peristaltic contractions in the esophagus allow food boluses to travel to the stomach, and their waves travel the length of the esophagus approximately every 9 seconds, at velocities of some one inch per second.

In the intestines, peristaltic movement is similarly slow and rhythmical. In abdominal distress due to simple indigestion, peristaltic movements are often accelerated. The device proposed herewith, sends ultra-low frequency stimuli to the abdominal viscera, thus signaling smooth muscles to regulate their pace. In this manner, intestinal harmony is more actively achieved than if simply left alone without prompting.

In this configuration, the device is apposed to the abdomen via a belt. The range of stimuli frequencies appropriate to this task approximates 0.1 HZ, ((or lower to encourage prompting).

The device's effectiveness is enhanced by techniques of concentration, visualization and meditation. By focusing mindful attention on the experiencing of the device's output, the reprogramming of the visceral nervous system is accelerated, and gastro-intestinal harmony is more efficiently achieved.

Regulating Neuro-Muscular Activity

Muscles and joints that have been stressed are physiologically overactive, and are prone to emitting higher intensities and frequencies of electrical muscle activity.

The ULF device 100 emits ultra-low frequency stimuli imparted to the muscles via direct apposition to the skin surface.

The ULF sensory signals imparted by the proposed device act to appease the over-activity of the said muscles, by coaxing their firing rates to more subdued levels.

The device's effectiveness is enhanced by techniques of concentration, visualization and meditation. By focusing mindful attention on the device's output, the down-regulation of the neuro-muscular nervous system is accelerated.

Stimulus Characteristics and Configurations

The following claims describe tactile stimuli configured to elicit selected mechanoreceptor skin responses. In addition, claims are made for the portion of the device that actually apposes itself to the skin surface of the subject, the interface. The present invention privileges the creation of tactile stimuli that are adapted to the physiology of the human skin, and to the properties of the nervous system, namely entrainment and coaxing.

Stimuli are imparted to skin tissues with varying degrees of energy. At lower settings, the force pressure is stimulating to a limited number of mechanoreceptors, mostly located in skin's surface layers. At higher pressure settings, it exerts influence on deeper connective tissues, muscles and joints. Light pressures, as in the first case, may be as low as 1 Gm/cm2; while in the second case, pressure may reach 250 Gm/cm2.

Lateral force measurements are important in stimuli that have horizontal movements. Force pressure is applied to the stimulus motion in order to displace tissues laterally. Lateral movements stimulate receptors containing mechanoreceptors sensitive to sideway motions. Horizontal displacement optimal for human skin spans from 1 mm to 1 cm.

The device is capable of generating vertical and horizontal stimuli. This allows for the stimulation of mechanoreceptors whose nerve roots respond to vertical, and horizontal compression. The amplitude displacement of these vertical pulses optimal for human skin may span from 0.5 mm to 5 mm. The device may be capable of circular motions, which offers mechanoreceptor stimulation in horizontal planes, or sinusoid movements, which creates mechanoreceptor stimulation in all vertical and all horizontal planes.

The interface element of the device may be made of materials that maximize touch receptor stimulation. Sensory loading and neural recruitment are thus augmented.

As described herein, the device 100 can be powered by a battery, which drives the microprocessor 200. The microprocessor 200 can be programmed to vary the frequency of the impulses to the solenoid actuator. In certain embodiment, frequencies can range from about 2 Hz to about 0.1 Hz. The microprocessor may be programmed to vary the amplitude, or power of the stimuli, from subliminal levels to clearly perceptible levels. Programmable, as well, is a timer that shuts off the device, or that turns it on at a future time.

The actuator translates the signals from the microprocessor into mechanical stimuli impacting the skin surface. A micro-solenoid converts the electrical signals into magnetic impulses, driving a weight or membrane to act upon the skin.

The stimulator is insulated with a rubberized or plastic envelope, for purposes of noise abatement and subject comfort.

One other visible component is an LED that emits light pulses in synchrony with the stimuli; an LCD (liquid crystal display) to display frequency, amplitude and timer functions, and control buttons.

Configurations of the Devices

The devices 100 can take several forms and configurations, among them:

1. A wristband. The components of the device, namely the microprocessor, the battery and the actuator are integrated into a wristband. Designed for nervous system stimulation via the wrist.
2. A headband. The device is integrated into a headband designed to provide contact of the actuator to the head's skin surface.
3. An ankle bracelet. The ankle bracelet works much like the wristband but is worn on the ankle.
4. A belt. The belt configuration provides contact of the actuator with abdominal skin.
5. The device may be incorporated into a pillow.

Device Utilization

In one mode of utilization, the device 100 can be attached to the wrist, the ankle, the head, or to the abdomen if in a belt configuration. Eyes closed, the patient gently centers attention on the stimuli produced by the device.

The individual wishing to drift to sleep allows the cadence of the stimuli to coax brainwaves into a progressive slow-down. A timer function allows for a 15-minute session during which time sleep may have occurred. With repeated use, the device's signals come to represent conditioned reflexes for sleep onset.

The individual wishing to normalize heart rate and blood pressure may choose to takes readings before using the device. The device is set at a frequency and amplitude that is indicated by a chart, predicated on the readings.

The device 100 can incorporate a pulse sensor and/or a blood pressure sensor whose readings are shown on a display. Certain models of the device 100 can display brain wave frequencies.

The device's effectiveness is enhanced by techniques of concentration, visualization and meditation. Focusing mindful attention on the experiencing of the device's output enhances the reprogramming of the nervous system; relaxation and sleep functions, cardio-vascular, muscular, and gastro-intestinal harmony are more efficiently achieved.

Consistent use of the device will, in time, lead to the establishment of conditioned reflexes that elicit the desired responses more quickly and automatically. The sleeper, for example, may find that his or her sleep onset time is greatly shortened with dedicated use of the device.

It will be appreciated that the device 100 of the present invention can include one or more of the following features: (a) have the capacity to generate mechanical stimuli to the skin that have sufficient energy so as to engage skin sensory receptors that convey their signals to the nervous system where the stimuli are consciously and/or subliminally perceived; (b) be capable of emitting these stimuli at frequencies that can be called ultra-low (i.e., frequencies between about 2 Hz (two per second) to 0.1 Hz, or one stimulus every 10 seconds); (c) invokes physiological and neurological principles called prompting and entrainment. A rhythmic stimulus will, under these physiological laws, promote synchronous physiological and neurological responses; (d) be capable of physiological coaxing—in this phenomenon, a stimulus may be presented with a much lower frequency than the desired physiological response, so that the said desired response is attained more quickly; (e) the presentation of ultra-low frequency rhythmic or paced stimuli to the skin which are, according to definitions of vibration, not vibratory, because they neither have a periodic motion, nor do they have a point of equilibrium. Moreover, they are of such low frequency that they lie below the lower ranges for what is commonly conceived as vibrational; (f) the microprocessor can be programmed to vary the amplitude, or power of the stimuli, from subliminal to clearly perceptible levels. Programmable, as well, is a timer that shuts off the device, or that turns it on at a future time; (g) optionally, the presentation of stimuli at irregular, or at patterned frequencies, or at gradually decreasing, or increasing frequencies; (h) the solenoid actuator translates the signals from the microprocessor into mechanical stimuli impacting skin surfaces. The micro-solenoid converts the electrical signals into magnetic impulses, driving a weight to act upon the skin. A rubberized or plastic membrane surrounds the actuator for purposes of noise abatement, and for enhancing subject comfort; (i) include an LED to emit light pulses in synchrony with the stimuli; an LCD (liquid crystal display) to show frequency, amplitude, and tinier functions, and control buttons; (j) the device may be activated and programmed through wireless technology such as Bluetooth; (k) the device may be applied to the skin surface anywhere on the body via any number of designs. One such variation includes a wristband configuration. Other designs make it possible for the device to be connected to the ankle, the chest, the abdomen, or to the head, among others; (l) the device may be incorporated into a pillow; (m) the impulses generated by the microprocessor are capable of driving different modalities of stimuli, either individually, or in combination. To augment neural recruitment of the tactile stimuli, other stimuli modalities may be paired synchronously with them. Multimodal stimuli increase the capacity of the device to regulate physiological processes such as sleep, blood pressure, heart rate, muscle relaxation, and gastro-intestinal centers in the nervous system, via the resonance of nervous system networks; (n) emit sounds—the rhythm frequency may, in addition to tactile stimuli, generate anyone of a number of sounds, or tones. A menu of pleasing sounds may be chosen such as waterfalls, waves, musical instruments, or electronically generated sounds; (o) emit light. The microprocessor may drive mini-lights. An LED (light emitting diode) or other light source, capable of being perceived by the user through closed eyelids, may be incorporated in the device. Color preferences may be selected; (p) provide electrophysiological stimulation. The microprocessor may drive an electrophysiological stimulation unit (ESU) that emits micro-currents, below the threshold of perception, or ones barely perceptible so as not to be distracting. These micro-currents, delivered via electro-conductive electrodes enhance the tactile stimuli's effects. Amperage, measured in microamperes (mA), may range from 1 to 100 mA. Electrical pulse width may range from 1 to 500 microseconds (μs); (q) the device can be utilized to reduce brain wave frequency. There are many physiological processes that are associated with slow brain waves. One of them is the promotion of relaxation and sleep. The device adapted to brain wave slowdown emits pulses ranging from 2 Hz to 0.2 Hz (or one impulse every 5 seconds). Brain wave slowdown may be produced by the device placed on the wrist, the ankle, or the head with apposition made possible by a headband; (r) the device can modulate blood pressure and regulating heart rate, utilizing stimuli that therapeutically entrain the nervous system. There is a relationship between pulse rate and blood pressure. In the case of hypertension, the device entrains the nervous system to relax the intensity and frequency of its signals to the vasculature. The invention's fundamental concept is that rhythmical stimuli, applied to the skin, have the capacity to regulate, via its nervous system circuitry, the pace of the heartbeat, and the tonicity of the body vasculature; (s) the ULF stimuli emitted by the device may thus be used to decrease blood pressure and heart rate. The range of the cardiac device's output spans from 1 Hz, or one cycle per second (reflecting a normal healthy heart rate of 60 beats per minute), to 0.2 Hz, or one stimulus per 5 seconds, which coaxes heart rate to normalize more quickly. A cardiac rhythm sensor may be connected to the user that displays the user's heart rate on the device. This provides visual biofeedback of cardiac rhythm. A blood pressure sensor that displays the user's blood pressure on the device. This provides visual biofeedback of the blood pressure; (t) the ULF stimuli emitted by the device may be used to harmonize gastro-intestinal function. The conditions potentially amenable to this approach may include gastric and duodenal ulcers and Crohn's disease. The range of stimuli emitted by the device reflects the frequencies found in normal peristalsis, namely one impulse every 5 to 10 seconds. The device configuration is that of a belt band; (u) the ULF stimuli emitted by the device may be used to regulate respiratory rate and rhythm, as in the treatment of certain types of hyperventilation; (v) the ULF stimuli emitted by the device may be used to provide neuro-muscular relaxation as, for example, in the treatment of overactive or injured muscles in sports; (w) the ULF stimuli emitted by the device may be used to encourage proper genito-urinary function, as in, for example, the treatment of the overactive bladder; and (x) the device's effectiveness is enhanced by techniques of concentration, visualization, and meditation. By directing mindful attention to the experience of the device's output, the reprogramming of the nervous system is accelerated, and desired physiological responses are more efficiently achieved. With repeated use of the device, its stimuli come to be established as conditioned reflexes that, with subsequent presentation, automatically produce their beneficial physiological effects.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claim.

What is claimed is:

1. An apparatus configured to generate and apply mechanical stimuli to skin of a user for regulating a physiological process comprising:
    a housing having a first surface for placement against the skin;
    an electro-mechanical actuator disposed within the housing and configured to generate and apply the mechanical stimuli to the skin;
    wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived.

2. The apparatus of claim 1, wherein the housing includes a fastener for detachably attaching the housing to a body of the user to allow the housing to be worn by the user.

3. The apparatus of claim 1, wherein the first surface comprises at least in part a membrane that is coupled to the electro-magnetic actuator, the membrane for placement against the skin and being configured to transmit the mechanical stimuli to the skin.

4. The apparatus of claim 3, wherein the membrane comprises a rubber membrane that is coupled to the electro-mechanical actuator such that movement of the electro-mechanical actuator is directly translated into movement of the membrane.

5. The apparatus of claim 1, wherein the electro-mechanical actuator comprises an electro-mechanical solenoid.

6. The apparatus of claim 1, further including a controller for controlling operation of the electro-mechanical actuator, the controller being configured to allow the user to change the frequency of the mechanical stimuli.

7. The apparatus of claim 6, wherein the controller includes a microprocessor that is operatively connected to a power supply and the electro-mechanical actuator.

8. The apparatus of claim 7, further including a user interface that is configured to permit the user to change one or more operating parameters including the frequency of the mechanical stimuli.

9. The apparatus of claim 8, wherein the operating parameters include an amplitude of the mechanical stimuli and a time period over which the mechanical stimuli are applied.

10. The apparatus of claim 1, wherein the mechanical stimuli have an amplitude between about 0.5 mm to about 5 mm.

11. The apparatus of claim 1, further including an LED to emit light pulses in synchrony with the mechanical stimuli.

12. The apparatus of claim 1, further including a sound generator and speaker through which sound is emitted for combination with the mechanical stimuli.

13. The apparatus of claim 1, wherein the apparatus is configured to regulating one or more physiological processes by performing one or more of the following actions: (a) slowing of brain waves; (b) inducing relaxation and sleep; (c) lowering of blood pressure; (d) slowing of heart rate; (e) normalizing of gastro-intestinal peristalsis; (f) pacing and slowing of respiratory rate; (g) modulating urinary bladder over-activity; and (h) alleviating muscular system over-activity.

14. The apparatus of claim 1, the actuator comprises a solenoid that converts electrical signals from a processor into magnetic impulses that physically drive a weight or membrane to act upon the skin.

15. The apparatus of claim 14, wherein the weight or membrane is insulated with a rubberized or plastic envelope for purposes of noise abatement and user comfort.

16. An apparatus configured to generate and apply mechanical stimuli to skin of a user for regulating a physiological process comprising:

a housing having a first surface for placement against the skin, wherein the first surface has an active region in which the mechanical stimuli are applied to the skin;

an electro-mechanical solenoid disposed within the housing and configured to generate and apply the mechanical stimuli to the skin;

a processor operatively connected to a power supply and to the electro-mechanical solenoid for sending command signals to the electro-mechanical solenoid to control operation thereof;

wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived.

17. The apparatus of claim 16, further including a user interface that is operatively connected to the processor and is configured to permit the user to input operating parameters, including the frequency and amplitude of the applied mechanical stimuli and a treatment time period which represents a duration of time over which the mechanical stimuli are applied.

18. A method for regulating a physiological process including the step of:

applying ultra-low frequency mechanical stimuli to skin of a person over a predetermined period of time, wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived.

19. The method of claim 18, wherein the step of applying the ultra-low frequency, non-vibratory stimuli to the skin comprises the step of generating and applying the ultra-low frequency mechanical stimuli using an electro-mechanical solenoid that is controlled by a processor both of which are contained within a housing that is configured for placement against the skin.

20. The method of claim 19, further including the step of emitting light pulses from a light source contained in the housing, the light pulses being emitted in synchrony with the application of the ultra-low frequency, non-vibratory stimuli to the skin.

21. The method of claim 19, further including the step of emitting sound from a speaker that is contained in the housing, the sound being emitted during application of the ultra-low frequency, non-vibratory stimuli.

* * * * *